US00PP35674P2

(12) United States Plant Patent
Hansen

(10) Patent No.: US PP35,674 P2
(45) Date of Patent: Mar. 5, 2024

(54) ***HIBISCUS* PLANT NAMED 'ALL EYES ON ME'**

(50) Latin Name: ***Hibiscus* hybrid (L.)**
Varietal Denomination: All Eyes on Me

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,448

(22) Filed: Aug. 22, 2023

(51) Int. Cl.
*A01H 5/02* (2018.01)
*A01H 6/60* (2018.01)

(52) U.S. Cl.
USPC ..... Plt./257

(58) Field of Classification Search
USPC ..... Plt./257
See application file for complete search history.

*Primary Examiner* — Susan McCormick Ewoldt

(57) ABSTRACT

A new and distinct cultivar of winter-hardy, herbaceous, perennial, hybrid *Hibiscus* plant named 'All Eyes on Me' comprising an upright and spreading mound habit of multiple, lightly branched, basal stems producing flowers starting in late July to early August and continuing for at least eight weeks. Flowers have overlapping petals of light pink with shiny reddish eye and short reddish veins. The back edge of the petals is corrugated or rippled providing extra strength to withstand heavy winds, rains, and sun. the foliage is three to five-lobed and dark-green-colored. The new plant is useful in the landscape as a specimen or in mass.

3 Drawing Sheets

Botanical classification: *Hibiscus* hybrid (L.).
Variety denomination: 'All Eyes on Me'.

STATEMENT REGARDING PRIOR DISCLOSURES UNDER 37 CFR 1.77(B)(6)

The first publicly released information of the new plant was on Dec. 1, 2022, when it was displayed with a photograph and brief non-enabling description on the website operated by Walters Gardens, Inc. The first offer for sale was on Sep. 6, 2022, and the first sale was made by Walters Gardens, Inc. on Mar. 6, 2023. Walters Gardens, Inc. obtained the new plant and all information relating thereto, from the inventor. No plants of *Hibiscus* 'All Eyes on Me' have been sold anywhere in the world, by any name, nor has any disclosure of the new plant been made more than one year prior to the filing date of this application, and such sale or disclosure within one year was either derived directly or indirectly from the inventor.

BACKGROUND AND ORIGIN OF THE PLANT

The present invention relates to the new and distinct hardy, herbaceous, *Hibiscus* plant, *Hibiscus* 'All Eyes on Me' hybridized under the direction of the inventor on Aug. 31, 2019, at a wholesale perennial nursery in Zeeland, Michigan. The new plant is a hybrid of the unreleased, proprietary hybrid known as 18-166-3 (not patented) as the female or seed parent and the unreleased, proprietary hybrid known as 16-134-2 (not patented) as the male or pollen parent. During the trial process, the new plant was assigned the breeder code labeled 19-275-3. Both parents have a complex mixture of species in them, comprising the species: *moscheutos, grandiflora, lasiocarpos*, and *coccineus*.

*Hibiscus* 'All Eyes on Me' was first asexually propagated in the late summer of 2020 by sterile shoot-tip tissue culture and later by shoot-tip cuttings at the same nursery in Zeeland, MI. The resultant asexually propagated plants have found both propagation methods to be stable and true to type in successive generations of asexual reproduction.

BRIEF SUMMARY OF THE PLANT

*Hibiscus* 'All Eyes on Me' differs from its parents as well as all other hardy herbaceous *Hibiscus* known to the applicant in many traits. The most similar *Hibiscus* known to the applicant are: 'Ballet Slippers' U.S. Plant Pat. No. 29,896, 'Dark Mystery' U.S. Plant Pat. No. 32,036, and 'Angel Eyes' U.S. Plant Pat. No. 35,355.

'Ballet Slippers' has a taller more upright habit, and the flowers are near white and blushed pink on the margins, with a smaller red eye, and without the red veining. 'Dark Mystery' has a larger habit with ovate deep mahogany-colored foliage and the red veining in the petals is more prominent. 'Angel Eyes' has a taller habit, the tri-lobed foliage is dark green, and the flower petals are near white with a shiny deep-red eye and raspberry-red veins and lack the corrugation or rippling of the back edge. 'All Eyes on Me' has more overlapping and ruffled petals than all the above-listed cultivars.

The female parent has a more open habit with flowers that are less puckered and the color was light pink. The male parent has a significantly shorter habit with fewer flowers that are red.

*Hibiscus* 'All Eyes on Me' is a unique hardy herbaceous *Hibiscus* with the following combined traits:

1. Winter-hardy compact perennial with an upright and spreading mound habit of multiple, well-branched, basal stems;
2. Many rotate flowers with overlapping, rippled petals of light pink with a shiny reddish eye and short reddish veins;

3. Back edge of the flower is corrugated or rippled providing extra strength to withstand heavy winds, rains, and sun;
4. Flowering beginning in late July to early August and continuing for at least eight weeks;
5. Three to five-lobed foliage of dark-green color.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source, and direction may cause the appearance of minor variations in color.

DETAILED BOTANICAL DESCRIPTION

Figure 1:
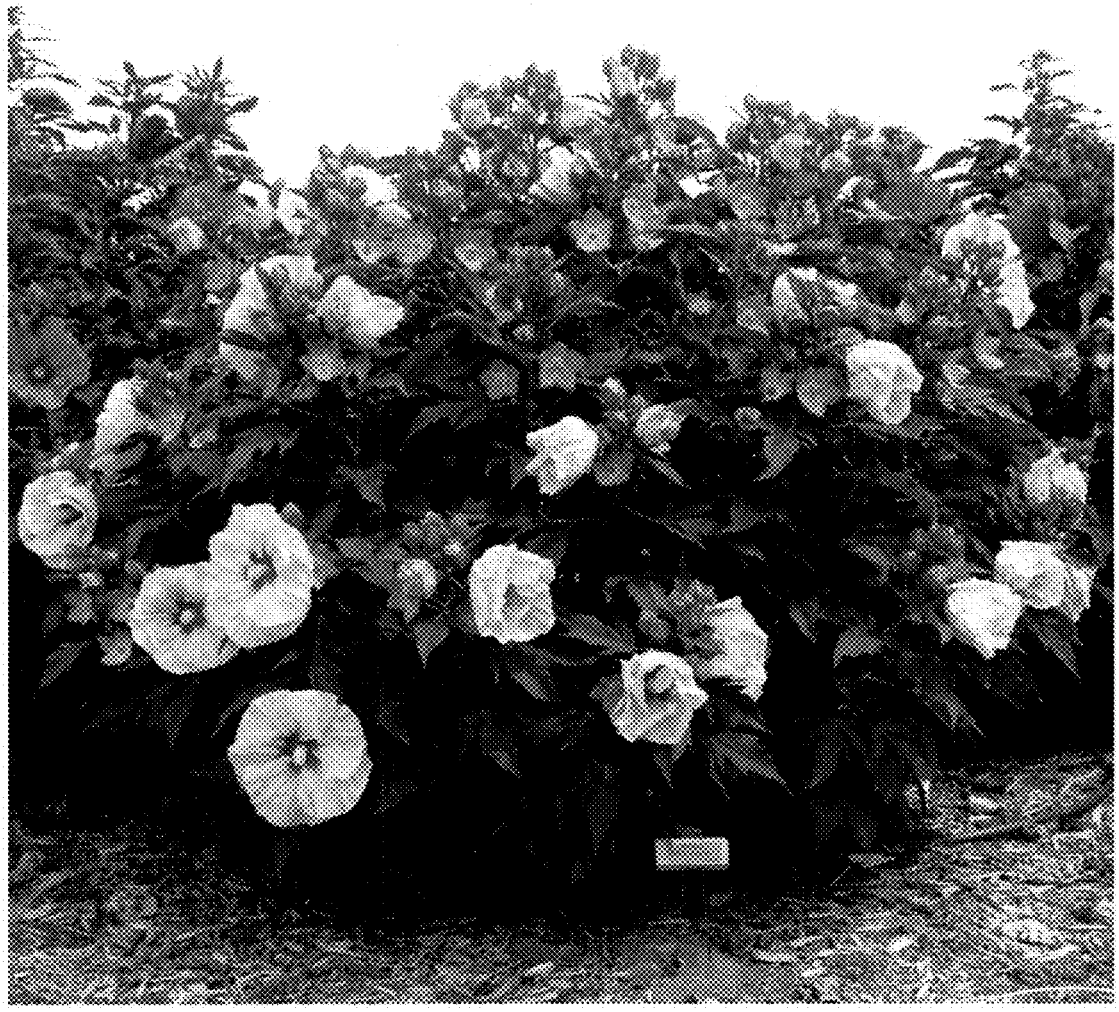
FIG. 1 shows a four-year-old plant in full flower in a display garden.
Figure 2:
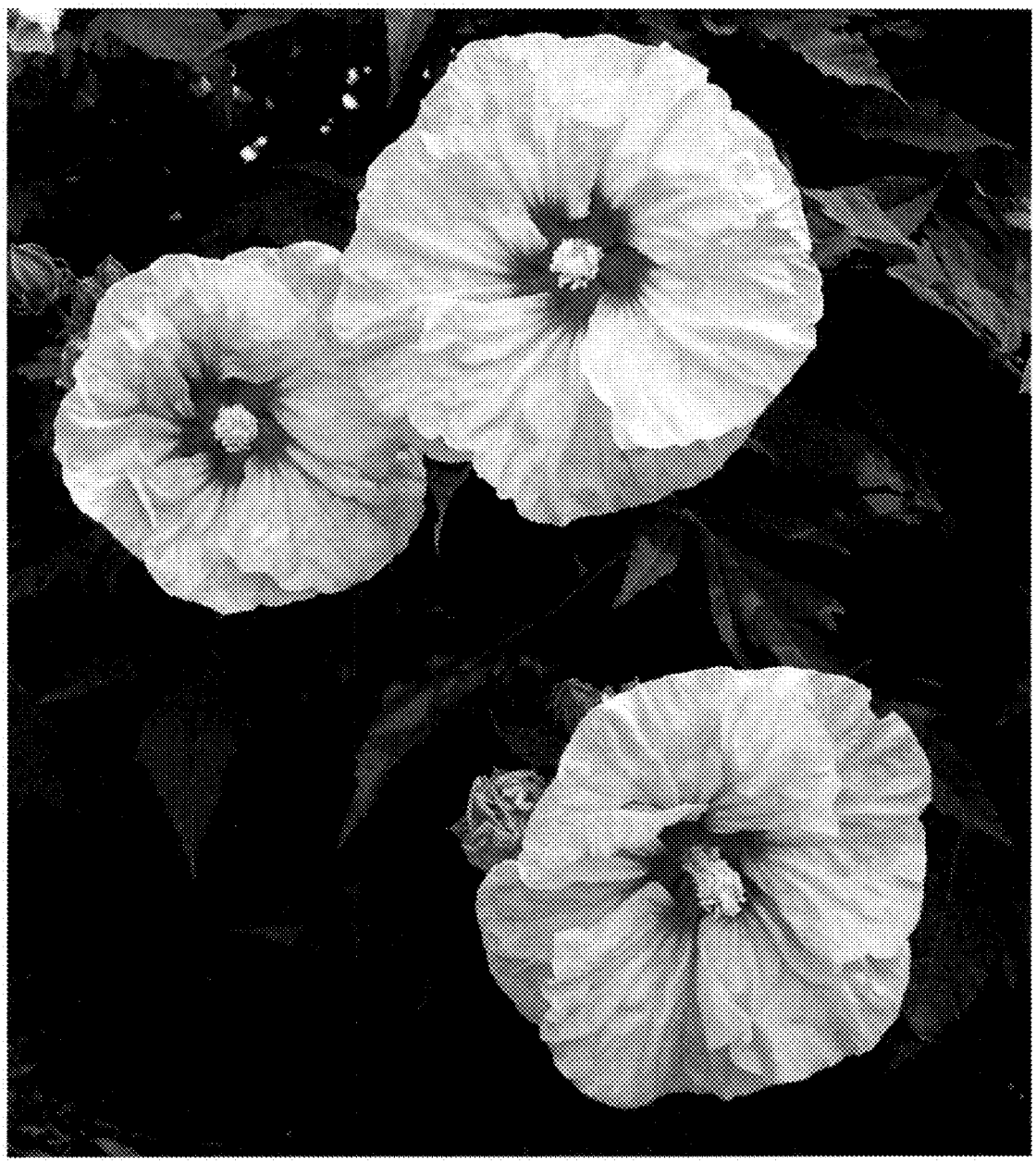
FIG. 2 shows a close-up of the flowers and bud.
Figure 3:
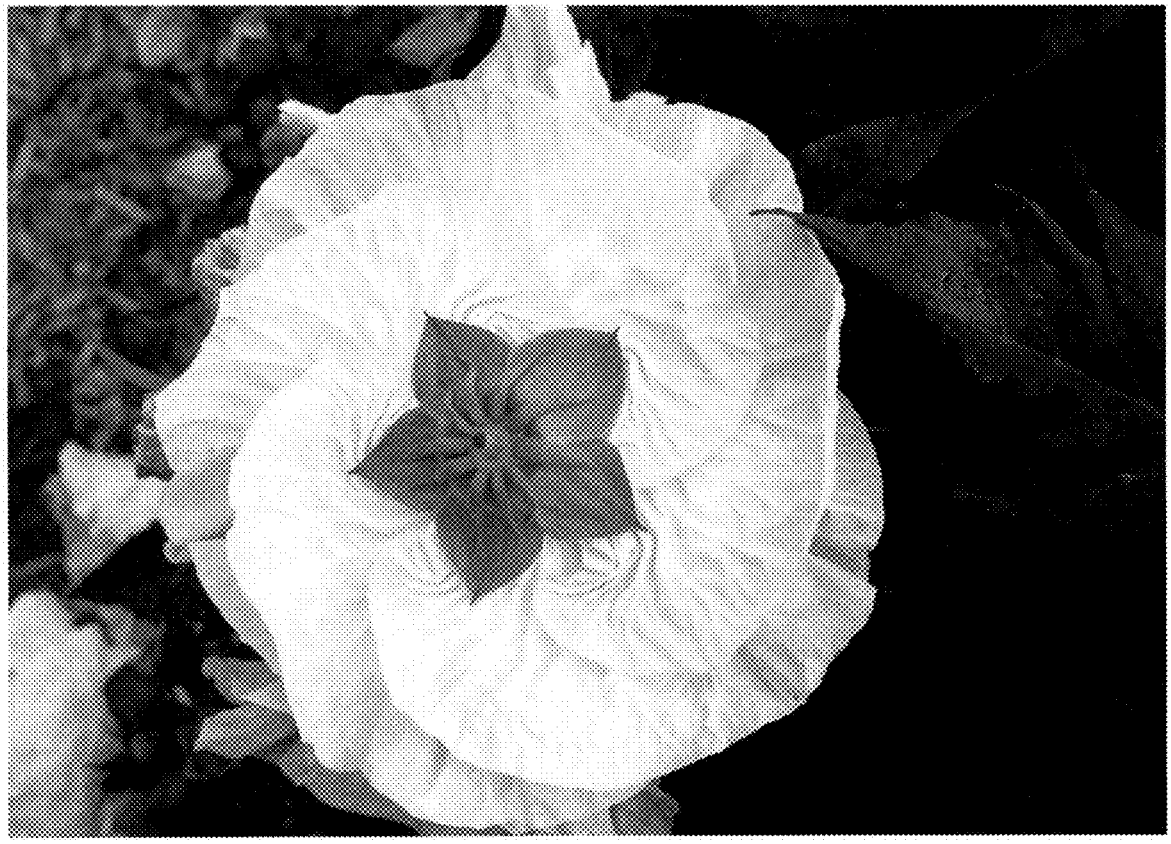
FIG. 3 shows the reverse of the flower with corrugated or rippled back edge of petals.

The following descriptions and color references are based on the 2015 edition of The Royal Horticultural Society Colour Chart except where common dictionary terms are used. The new plant, *Hibiscus* 'All Eyes on Me', has not been observed in all possible environments. The phenotype may vary slightly with different environmental conditions, such as temperature, light, fertility, moisture, and maturity levels, but without any change in the genotype. The following observations and size descriptions are of three-year-old plants in the loamy-sand, full-sun display garden of a nursery in Zeeland, MI with supplemental fertilizer and water as needed. The plants are of natural habit and were not treated with plant growth regulators, nor were they pinched at any time in the growth year.

Parentage: The female or seed parent is the unreleased, non-patented, proprietary *Hibiscus* known by the breeder code 18-166-3, the male or pollen parent is the unreleased, non-patented, proprietary *Hibiscus* known by the breeder code 16-134-2;

Propagation:

*Method*.—Shoot tip cuttings and sterile shoot-tip plant tissue culture division.

*Time to initiate roots from tissue culture*.—About two weeks.

*Rooting habit*.—Normal, branching, developing thick to about 2.2 cm diameter, fleshy; root color creamy yellow nearest RHS 161D depending on soil type.

*Crop time*.—Under normal summer growing conditions 12 to 16 weeks to flower in a four-liter container from cutting. Plant vigor is very good.

Plant description:

*Plant habit*.—Hardy herbaceous perennial with about 54 thick, mostly upright, lightly branched stems producing an upright and spreading mound to about 125 cm tall and about 165 cm wide; flowering in distal one-third of plant with up to about 26 flowers per main stem, average flowers per stem about 20.

*Stem*.—Cylindrical, glabrous, glaucous; to about 125 cm tall and about 19 mm diameter at base, average about 105 cm tall and about 13 mm diameter at base; branched.

*Stem color*.—Between RHS 146D and RHS 148C, without anthocyanins.

*Branches*.—To 4 per stem, average about 3 per stem; cylindrical, glabrous, glaucous; to about 9 cm long and 2.5 mm diameter at base, smaller distally.

*Lateral branch color*.—Between RHS 146D and RHS 148C, without anthocyanins.

*Internode*.—About 20 nodes per stem below single flowers; average 40 nodes per stem; internode length about 3.1 cm of unpinched plant.

*Internode color*.—Same as surrounding stem.

Foliage description: Palmately tri-lobed to peta-lobed, with lobes of varying lengths; alternate; coarsely and irregularly dentate; apex and side lobes acute; base cordate; micro-puberulent and matte both abaxial and adaxial; moderately to deeply incised, with lobes from 2.5 cm to 7 cm deep, with some incised to petiole;

*Leaf blade size*.—To about 16 cm long and about 13 cm across, average blade size 12.5 cm long and 9 cm wide; no fragrance detected.

*Foliage color*.—Young expanding leaves — adaxial nearest RHS 137C with slight anthocyanin blush of nearest RHS N187A, abaxial nearest RHS 148B; mature leaves — adaxial nearest RHS NN137C, abaxial between RHS 148A and RHS 148B.

*Veins*.—Palmate; matte and micro-puberulent both adaxial and abaxial; costate on abaxial.

*Vein color*.—Adaxial primary proximal veins between RHS 145A and RHS 146D in basal 15 cm, secondary and distal primary veins between RHS 148B and RHS 148C with moderate blush of nearest RHS 184A; abaxial veins variable, proximal midrib and primary veins nearest RHS 146D, distal primary veins nearest RHS 148B with moderate blush to solid nearest RHS N186C with more light exposure.

*Petioles*.—Mostly cylindrical, proximally slightly applanate on adaxial side near base; sparsely micro-puberulent; to about 10.5 cm long and 5 mm across at base, average size about 8 cm long and 4 mm wide at base.

*Petiole color*.—Adaxial and abaxial nearest RHS 146D maculate with a light blush of nearest RHS N186C.

Flower description: Complete; perfect; actinomorphic; rotate; solitary; mostly outwardly facing; slightly cupped;

*Flower size*.—To about 18 cm across and 6 cm deep, decreasing distally; dark red shiny eye medium width, about 5 cm across; smaller later in the season.

*Buds one day prior to anthesis*.—Ellipsoidal with flattened apex and bluntly truncate base; sepals adpressed to petals; to about 5.5 cm long and about 4.5 cm diameter near middle.

*Bud color one day prior to anthesis*.—Exposed petal color central portion nearest RHS 49C, distal margin between RHS N57D and RHS 62A, with distal veins nearest RHS 61C and proximal veins lightening to nearest 64C, calyx nearest RHS 146B.

*Epicalyx*.—Average about 10 per flower; linear; entire, margin micro-ciliolate; micro-puberulent abaxial and adaxial; sharply acute apex and truncate base, arcuate upwards near apex; to about 25 mm long and about 4 mm wide at base.

*Epicalyx color*.—Adaxial nearest RHS 146C and abaxial nearest RHS 137B without anthocyanins.

*Calyx*.—Campanulate, forming a broad star-shaped hypanthium; to about 15 mm deep and 70 mm wide at apices.

*Sepals*.—Typically, five; ovate; acuminate apex; margin entire, edentate; adaxial and abaxial micro-puberulent and matte; about 38 mm long, about 26 mm wide at fusion, basal 19 mm fused.

*Sepal color*.—Adaxial proximal portion nearest RHS 147C, distal portion nearest RHS 147B with veins nearest RHS 145C; abaxial nearest RHS 137B; without anthocyanin blush.

*Inflorescence*.—Up to 26 per main stem and branches without pinching.

*Flower lastingness*.—Individually persist for one to two days; effective for at least 8 weeks beginning late July to early August.

*Flower fragrance*.—No detectable fragrance.

*Petals*.—Five; glabrous adaxial and abaxial; adaxial eye zone lustrous, distal adaxial portion and entire abaxial matte; adnate to the androecium to form a column, imbricate to about 120% overlapping at widest part (petals overlapping both petals on either side, so three petals are stacked about 20%); strongly undulate; palmately veined, primary veins slightly impressed on adaxial and slightly costate abaxial; surface mostly flat; apex rounded with distinct basal claw and limb; margins entire, edentate; leading edge slightly folded under itself; corrugated, or rippled in back edge providing extra strength to withstand heavy wind, rain, and sun.

*Petal size*.—Average about 14 cm across and about 10 cm long, claw base about 9 mm across.

*Petal color*.—Adaxial basal 15 mm nearest RHS 46B, distal 10 mm of eye between RHS 60A and 53A, outer portion between RHS 69A and RHS 69B with distal veins nearest RHS 73B transitioning from between RHS 60A and 53A extending from eye zone; abaxial basal 14 mm nearest RHS NN155A, distal portion lighter than RHS 65D and where petal is folded nearest RHS 65B, abaxial veins nearest surrounding tissue;

*Gynoecium*.—Single; partially enclosed in column. Column: glabrous and lustrous; about 31 mm long and about 13 mm across at base; with pistil exserted about 17 mm; Column color: nearest RHS NN155B; Style: micro-puberulent in region exserted above column; about 37 mm long, penta-furcate in about distal 7 mm, branch diameter about 1 mm; color nearest RHS NN155A in exposed portion, and RHS 11D portion enclosed in column; Stigma: typically, five; flattened globose, puberulent, about 3 mm in diameter and 1.5 mm tall; color in nearest RHS 160D; Ovary: superior; globose, longitudinally grooved in undulated pattern; acute apex, and truncate base; about 11 mm across at base and about 7 mm tall; color between RHS 150D and RHS 145D.

*Androecium*.—Attached to column. Filaments: numerous, about 100, attached starting about 3 mm from base to 2 mm from apex of column; to about 6 mm long, about 0.2 mm diameter; color nearest RHS N155C; Anthers: flattened reniform; dorsifixed; about 2 mm across, 2 mm long, and about 1 mm thick; color nearest RHS 4D; Pollen: abundant, globose, less than 0.1mm across; color nearest RHS 11C.

Pedicel: Cylindrical, micro-puberulent in proximal and distal portions; slightly glaucous; length from base of sepal to abscission point about 1.7 cm long, from abscission point to stem node about 7.7 cm long; about 3 mm wide; longer on early flowers and decreasing in distal flowers;

Pedicel color: Nearest RHS 146D proximal abscission point, and nearest RHS 146D;

Peduncle: Cylindrical, glabrous, glaucous; flowering portion to about 30 cm tall and about 10 mm diameter at base, average about 28 cm tall and about 9 mm diameter at base;

Peduncle color: Between RHS 146D and RHS 148C, without anthocyanins; Fruit and seed: not yet observed;

Resistance: *Hibiscus* 'All Eyes on Me' has not displayed any pest and disease resistance beyond that typical of hardy perennial *Hibiscus*. The plant grows best with plenty of moisture. Hardiness at least from USDA zone 4 through 9.

I claim:

1. A new cultivar of hardy herbaceous perennial *Hibiscus* hybrid plant named 'All Eyes on Me' as herein illustrated and described.

* * * * *